United States Patent [19]
Allen

[11] Patent Number: 5,667,516
[45] Date of Patent: Sep. 16, 1997

[54] MECHANISM FOR CUTTING AN UMBILICAL CORD

[76] Inventor: Sean A. Allen, 142 Sheldon St., El Segundo, Calif. 90245

[21] Appl. No.: 432,218

[22] Filed: May 1, 1995

[51] Int. Cl.$^6$ .................................................. A61B 17/42
[52] U.S. Cl. .................... 606/120; 606/174; 606/142
[58] Field of Search .................... 606/120, 142, 606/174; 128/305, 346, 319, 320; 30/136, 124

[56] References Cited

U.S. PATENT DOCUMENTS

| | | | |
|---|---|---|---|
| 4,648,401 | 3/1987 | Mattson | 606/120 |
| 4,938,215 | 7/1990 | Schulman et al. | 606/120 |

*Primary Examiner*—Michael Powell Buiz
*Assistant Examiner*—Kevin Truong

[57] ABSTRACT

A disposal device for clamping, cutting and taking blood samples from an unbilical cord of a newly born infant. When the device is closed around an umbilical cord the cord is compressed and two separate pairs of clamping jaws are locked onto the cord. Further compression of the device severs the cord between two clamps and ejects the clamp which retains the infant's end of the unbilical cord. The jaws holding the mother's end of the cord can be opened enough to allow blood samples to be taken while still holding the cord firmly. The present invention comprises a double jaw clamping mechanism which incorporates a releasable locking means, a double jaw fetal end cord clamp which separates from the body of the device and remains locked to the fetal end of the cord, and a hinged holder containing a blade for severing the cord.

8 Claims, 5 Drawing Sheets

MECHANISM FOR CUTTING AN UMBILICAL CORD

BACKGROUND OF THE INVENTION

1. Field of the Invention

This invention relates to a clamping and cutting mechanism, particularly a mechanism for clamping an umbilical cord at two spaced points, cutting the cord between the two clamp points, and partially unclamping one of the severed cord sections so that blood samples can be taken.

2. Prior Developments

In the practice of delivering a newborn infant it is necessary to sever the umbilical cord, i.e. a tubular membrane containing the arteries and vein which supply oxygen and nutrient enriched blood from the mother to the fetus and which carries waste products from the fetus back to the mother. As blood flows through the umbilical cord, it is essential that the cord be sealed on both sides of where it is to be severed before any cutting takes place. The conventional method to clamp and cut the umbilical cord is a four step procedure. To accomplish this task the doctor must clamp one hemostat (a locking scissors like instrument) onto the umbilical cord, obtain another hemostat and clamp it on the cord a few inches away. After the two clamps are set, the doctor obtains a pair of scissors and warns the staff that he/she is about to cut so that they can avoid being sprayed by blood. The doctor then cuts the cord between the two clamps with a pair of scissors.

When the two hemostats are locked onto the cord, a bubble of blood forms in the segment of cord between the two clamps. When this segment is cut, blood tends to spray and often strikes the medical staff. Clamping and cutting the umbilical cord by the conventional method while trying to hold a slippery squirming infant in gloved hands can prove to be a challenge. If the infant has any abnormalities or health problems, the procedural difficulties are magnified, making speed and efficiency critical.

After the cord has been cut the number of arteries and veins in the cord are counted, and blood samples are obtained from the mother's end of the cord. In order to count the number of arteries and veins the doctor simply looks at the free end of the cord. If the end of the cord does not have a clean cut, it is sometimes necessary to make another cut in the cord in order to get a better view. The blood sample is obtained from the cord by placing a test tube in alignment with the free end of the cord and opening the hemostat enough to allow blood to flow into the test tube. During this procedure blood often sprays on the medical staff due to the cord slipping out of the jaws of the hemostat or by misdirection of the artery when the hemostat jaws are opened. After enough blood is obtained, the hemostat is reclamped. The hemostat stays attached to the umbilical cord until after the placenta is extracted from the mother. The hemostat on the infant end of the umbilical cord is replaced by a disposable plastic clamp which stays with the baby until the umbilical cord falls off.

It is the object of the present invention to speed up the clamping and cutting procedure in order to provide the doctor with more time to focus on and administer to the needs of the patients and to protect the medical staff from blood transmitted disease such as H.I.V. and Hepatitis. The present invention includes a clamp section system design so that when it is compressed around the umbilical cord the cord is clamped in two places; both clamps are locked closed before any cutting takes place, and the blood is squeezed out of the clamped-off section to eliminate the possibility of blood become air borne when the cord is cut. The blade is concealed in the body of the mechanism to eliminate the possibility of anyone being injured by the blade. The mechanism of the present invention is designed so that it can be used to draw blood from the cord in a controlled manner, and to provide a cleanly severed end on the fetal side of the umbilical cord, with sufficient length to view the number of arteries and veins in the cord.

In the recent past, various umbilical cord clamping and cutting devices have been designed to speed up the clamping and cutting process. Known devices intended to perform cutting and clamping tasks are disclosed in U.S. Pat. Nos. 5,190,556, Hessel, 5,127,915, Mattson, 5,009,657, Cotey et al, 4,870,965, Jahanger, and 4,648,401, Mattson. None of these insure that the cord is fully sealed before cutting begins, or that the cord will not slide out when cutting without puncturing the cord. Also, U.S. Pat. Nos. 4,938,215 Schulman et al., 4,856,517, Collins et al., 4,781,188, Collins et al., 4,781,188, Collins, 4,716,886, Schulman et al, 4,572, 181, Mattler, 4,428,374, Auburn, 4,026,294, Mattler, 3,631, 858, Ersek, 3,323,208, Hurley, 3,166,071, Mayer, 3,106, 919, Churchville, 2,524,337, Whittaker, and 2,060,724, Carrol all show umbilical cord clamp and cutting devices. Of these Patents, none allow the maternal clamp to be opened for the taking of blood samples. The devices of these patents have generally failed to meet all of the needs of the doctor and the patients.

U.S. Pat. No. 4,212,303, issued to John Nolan on Jul. 15, 1980, discloses an umbilical cord clamp that comprises two clamp arms hingedly connected together for closure on the cord. The free end of one clamp arm has a deflectable tongue that is lockable in a recess in the free end of the other arm when the clamp arms are closed on the umbilical cord.

U.S. Pat. No. 4,716,886 to Schulman et al, discloses an umbilical cord cutting device that includes two similarly constructed clamps connected together by a shear pin. A cutting blade is floatably positioned between the clamps so that when the clamps are clamped to the umbilical cord the blade can be moved through the space between the clamps to sever the cord and the shear pin, thereby separating the clamps.

U.S. Pat. No. 4,856,517, issued to J. Collins et al on Aug. 15, 1989, discloses an umbilical cord cutter mechanism that include a holder containing a cutter blade and two detachable clamps on opposite sides of the blade. Each clamp has latch means for holding the clamp in the closed position when the holder is closed to operate the blade. The holder can be removed from the clamps after the cord severing operation.

There is apparently no provision in the device of U.S. Pat. No. 4,856,517 for partially loosening either clamp to withdraw a blood sample from one of the severed cord sections.

U.S. Pat. No. 4,870,965, issued to M. Johanger, discloses an umbilical cord severing mechanism wherein a scissors cutter has a first cord clamp affixed to the cutter structure, and a second fetal cord clamp detachably mounted in the cutter structure, whereby the fetal clamp is ejected during the cutting stroke. A leaf spring in the cutter structure acts as an ejector device. The cutting action is achieved by two blade elements carried by the opposed jaws of the scissors structure.

One disadvantage of the patented structure is that the blades begin the cutting operation before the umbilical cord is fully clamped in the two clamp mechanisms. Also, there is no provision for relaxing the clamp pressure on the severed cord to facilitate drawing a blood sample.

U.S. Pat. No. 5,009,657, to J. Cotey et al, shows an umbilical cord cutting mechanism that includes a jaw structure having an integral cutter blade and a separable fetal chord clip. The jaw structure includes a hinge structure that has a lug that normally holds the fetal chord clip in the jaw structure; when the jaw structure is closed the lug is displaced so that the fetal chord clip can separate from the jaw structure.

U.S. Pat. No. 5,127,915 to P. D. Mattson, discloses a scissors type instrument for cutting an umbilical cord, said instrument having a detachable clamp structure equipped with a latch means so that after the cord is severed the clamp remains attached to the infant end of the cord. The scissors type instrument can be removed from the clamp structure after the cord-severing operation.

One disadvantage of the arrangement of U.S. Pat. No. 5,127,915 is that the cord is clamped at only one point along the cord surface; the cord is thus not fully compressed in the immediate vicinity of the cutting plane so that there is a danger of blood spurting from the unclamped end of the cord. The unclamped end of the severed cord is not sealed.

SUMMARY OF THE INVENTION

The present invention contemplates an umbilical cord cutting mechanism, wherein the cord is fully clamped in two places before the cutter blade is moved to sever the cord. The aim is to insure that the cord will be in a relatively flat compressed condition containing minimal quantities of blood when the cutting operation begins.

A further feature of the invention is an adjustable latch system that allows the clamp on the maternal end of the cord to be partially loosened whereby blood samples can be taken from the severed maternal cord section while the cord is still in a clamped condition.

An additional feature of the invention is a fetal cord clamp that is removably disposed in the main clamp housing so that its cord grip plane is spaced from the blade cutting plane. This feature enables the fetal cord to have a terminal section that is uncompressed, whereby arteries and veins in the cord section can be easily examined.

It is a principal aim of the present invention to firstly increase the care being given to the patient by reducing the number of unnecessary distractions of the doctor, and furnishing the doctor with more time to care for the patient. Secondly, it is an aim of the invention to decrease the possibility of the medical staff being infected by a blood transmitted disease, such as H.I.V. or Hepatitis, by reducing the amount of blood loss from the umbilical cord, eliminating cord blood from becoming airborne and eliminating the possibility of injury by the cutting blade. Thirdly, it is an aim of the invention to reduce the possibility of infection to patients by eliminating the possibility of external blood and bacteria entering the patient's bloodstream through the cord where the cord is cut. And lastly, the invention seeks to minimize the number of instruments needed to perform the procedure, thus reducing the number of instruments needed to be handled and cleaned.

The present invention relates to a clamping and cutting device that comprises a double jaw clamping mechanism which incorporates a releasable locking means, a double jaw fetal end cord clamp which separates from the body of the device and remains locked to the fetal end of the cord, and a hinged holder containing a blade for severing the cord through a secondary action.

The functions and processes carried out by the present invention are simple and direct. The cord is fitted through the opening of the device until it clears the locking mechanism. By squeezing the upper and lower arms of the clamp together the device closes around the cord, compressing it and sealing the cord in two places. Further squeezing pressure forces the cutting blade upward through the segments of the cord between the two pairs of clamping jaws that are locked onto the cord. As the blade is severing the cord wedge along side the blade applies force to the clamp which is locked to the infant's end of the cord, causing it to eject out of the device. This completes the separation of infant from mother. In order to take blood samples from the placenta, a collection tube is inserted into the side of the device which holds the mother's end of the cord; the jaws of the device can be partially opened by the application of forward pressure on a release lever to facilitate the collection of the blood sample. The jaws can be opened enough to allow blood to flow out of the cord, but not enough to allow the cord to slip out of the jaws of the device. When enough blood has been taken from the placenta the cord can be resealed by squeezing the device into the locked position thus stopping the flow of blood through the cord.

Further structural details and operational details of the invention will be apparent from the attached drawings and accompanying description of the mechanisms shown in the drawings.

THE DRAWINGS

Figure 9:
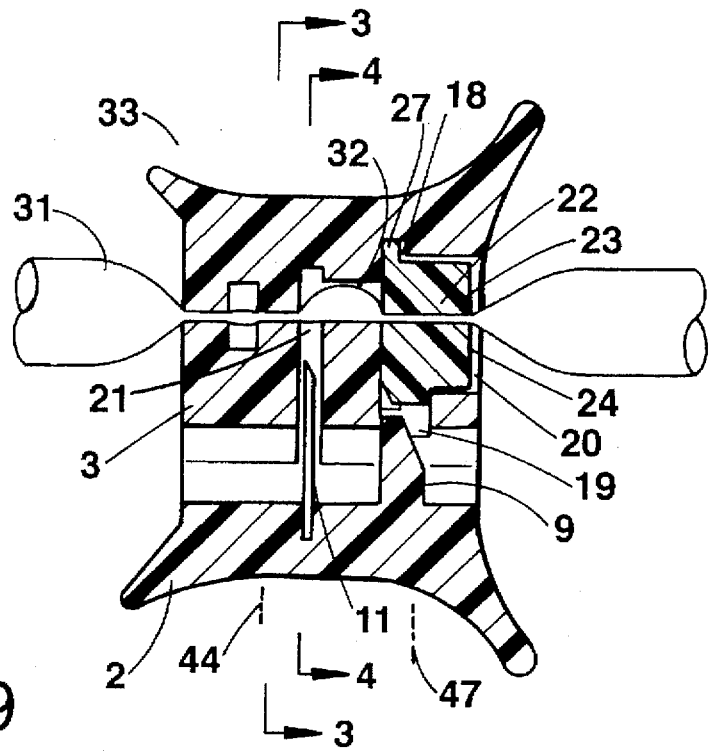
Figure 10:
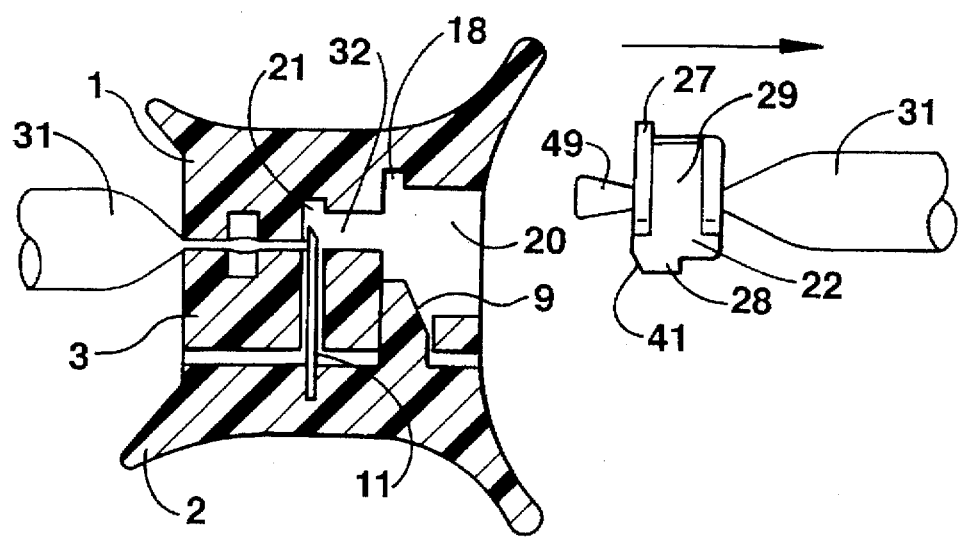

FIGS. 9 and 10 are transverse sectional views taken through the mechanism. FIG. 9 shows the mechanism in a closed position prior to a cord severing operation. FIG. 10 shows the mechanism after the cord has been severed and the fetal cord clamp has been separated from the mechanism.

DESCRIPTION OF A PREFERRED EMBODIMENT OF THE INVENTION

The drawings show a mechanism for cutting an umbilical cord 31 into two sections, namely a cord section attached to the mother and a fetal cord section attached to the new born infant. FIG. 9 shows the umbilical cord prior to the cutting operation, whereas FIG. 10 shows the condition after the cord cutting operation. In FIG. 10 the fetal section (attached to the infant) has a fetal cord clamp 22 attached thereto; the maternal cord section is attached to the clamping mechanism designated generally by numeral 33. During the cord cutting operation the fetal cord clamp 22 is ejected out of mechanism 33 in a generally rightward direction, as viewed in FIGS. 9 and 10.

Figure 1:
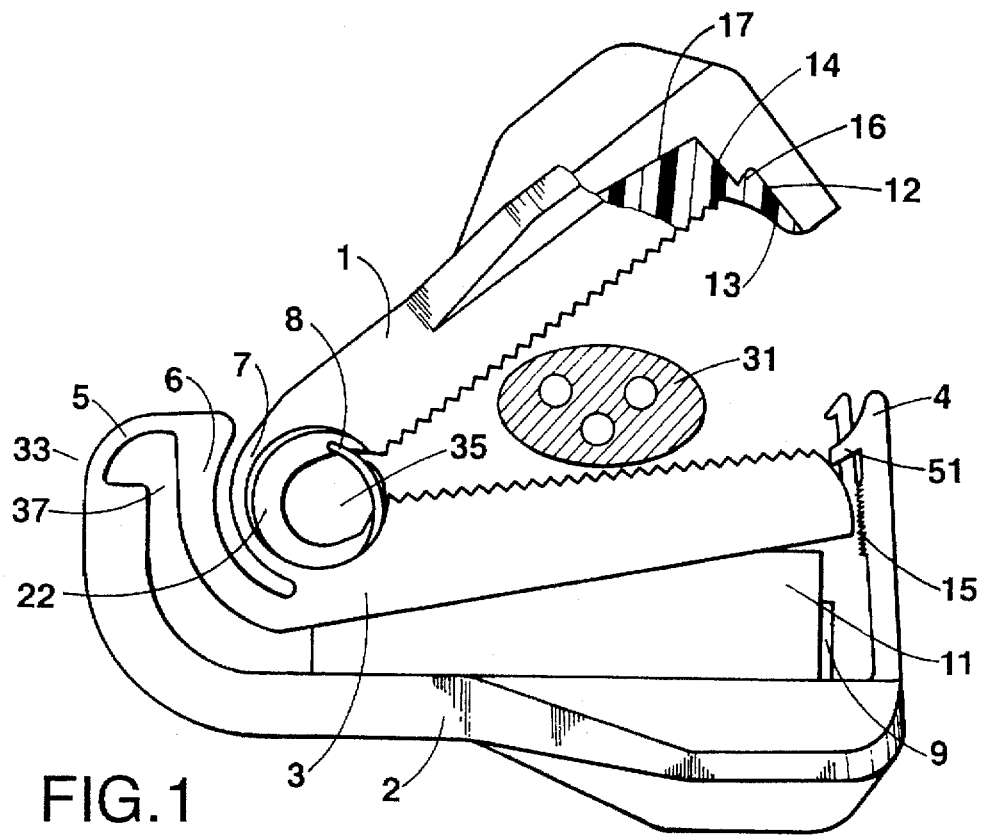
FIG. 1 is a side elevational view of a cutting and clamping mechanism embodying the invention.
Figure 2:
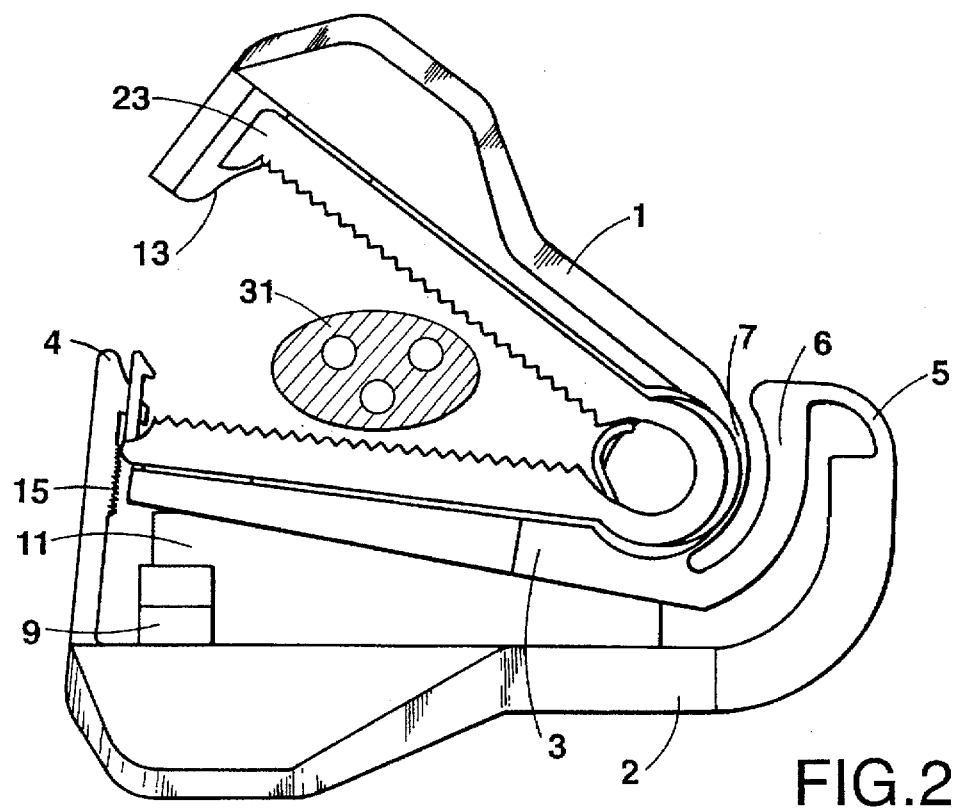
FIG. 2 is a second side elevational view of the FIG. 1 mechanism, taken from the other side of the mechanism.
Figure 3:
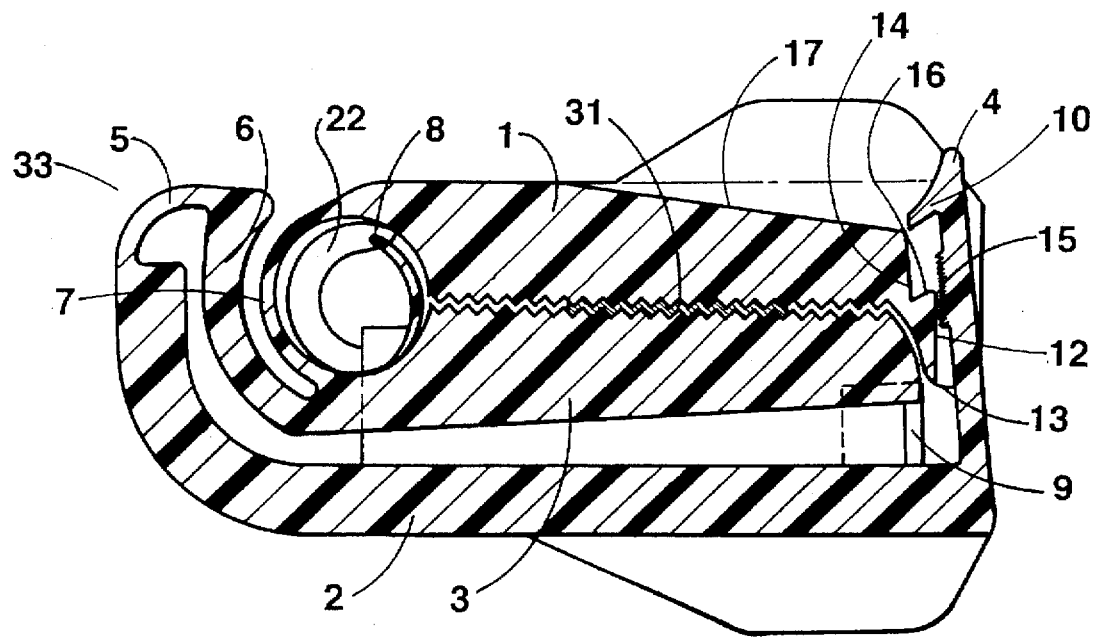
FIG. 3 is a sectional view of the FIG. 1 mechanism, taken generally on line 3—3 in FIG. 9.

FIGS. 1, 2 and 3 show the general features of clamping mechanism 33. As there shown, the clamping mechanism comprises a first jaw 1 and a second jaw 3 hingedly joined together by a flexible wall type hinge. This hinge is shown as an arcuate wall 7 integral with jaws 1 and 3, and centered generally around an imaginary hinge axis 35. The arcuate length of wall 7 is approximately one hundred thirty degrees, measured around axis 35.

Arcuate hinge wall 7 is integral with a relatively thick rigid connector wall 6 that joins wall 7 to a second arcuate wall 5 centered on an imaginary hinge axis 37. Arcuate wall 5 has an arcuate length that measures about ninety degrees, taken around axis 37.

Arcuate wall 5 has a lesser length than arcuate wall 7. Also, arcuate wall 5 is somewhat thicker than arcuate wall 7, such that hinge wall 7 has a greater flexibility than hinge wall 5. Wall 6 is essentially non-flexible.

Arcuate wall 7 forms a hinge that enables jaw 1 to pivot toward or away from jaw 3 around hinge axis 35. Arcuate wall 5 forms a second hinge that enables an elongated blade holder arm structure 2 to pivot (or swing) toward or away from jaw 3. The two hinge structures are connected to the common connector wall 6.

FIGS. 1 and 2 show the jaw structure in an open position whereby the mechanism can be moved to partially encircle the umbilical cord 31. FIG. 3 shows the jaw structure closed on the umbilical cord 31; jaw 1 is moved downwardly toward jaw 3 to a position wherein the clamped umbilical cord 31 is located slightly above the sharpened edge 39 of a cutter blade 11. Blade edge 39 appears in FIG. 4. Blade 11 is suitably anchored in holder (arm structure) 2.

The aforementioned fetal cord clamp 22 (shown in FIGS. 7 and 8) is removably disposed in mechanism 33 so that cord gripper elements 23 and 24 of the clamp move generally in synchronism with jaws 1 and 3. Thus, as jaw 1 moves toward jaw 3 the corresponding gripper element 23 moves toward gripper element 24. When the jaws are in the FIG. 3 closed position clamped on the umbilical cord, the corresponding gripper elements 23 and 24 will be in gripping engagement with the umbilical cord (but in a different gripper plane).

Figure 7:
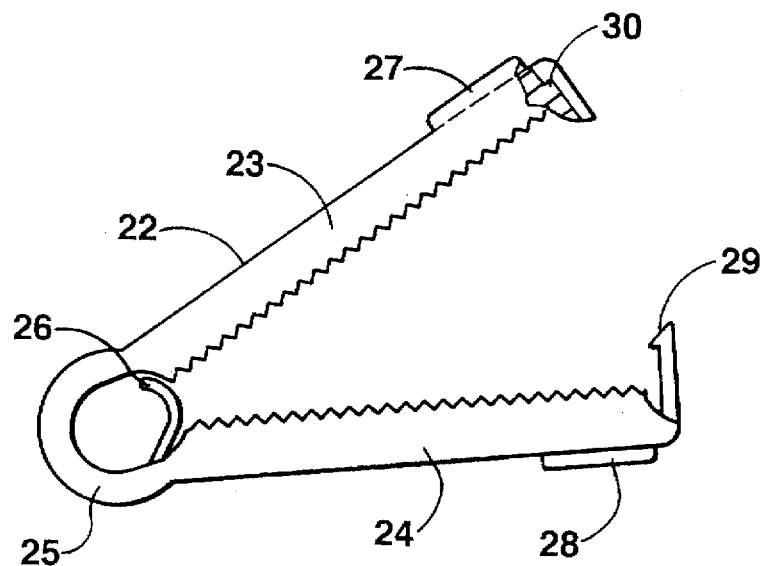
FIG. 7 is a side elevational view of a fetal cord clamp used in the FIG. 1 mechanism.
Figure 8:
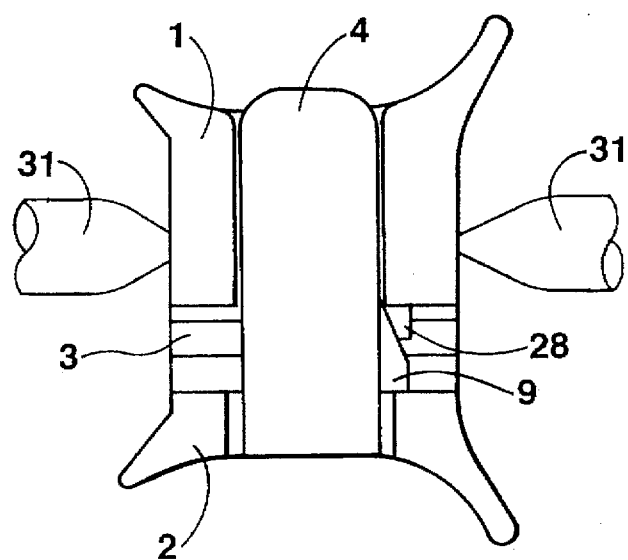
FIG. 8 is an end view of the FIG. 1 mechanism, with the mechanism in a closed condition.

FIG. 7 shows some features of fetal cord clamp 22. As there shown, the clamp comprises an arcuate hinge wall 25 joining the two elongated gripper elements 23 and 24. The free end of the gripper element 24 has a latch arm 29 that is adapted to lockably engage a shoulder 30 on gripper element 23 when the mechanism is in the FIG. 3 condition, i.e. when jaw 1 is closed onto jaw 3, and gripper element 23 is closed onto gripper element 24.

Clamp 22 is removably disposed in mechanism 33 by positioning the arcute hinge wall 25 within the circular packet 20 formed by arcuate wall 7 pocket 20 appears in FIGS. 9 and 10. Wall 7 partially surrounds wall 25 to retain clamp 22 in mechanism 33. Additionally, as shown in FIG. 10, gripper element 25 of the fetal cord clamp has a lug 27 thereon that is adapted to fit into a slot 18 formed in jaw 1. FIG. 9 shows generally how clamp 22 fits within a cavity in the right side of jaw 1. Gripper element 24 has a lug 28 (FIGS. 7 and 10) that registers with an upstanding wedge element 9 carried on lower jaw 3, such that when jaw 1 is moved downwardly a predetermined distance the wedge element exerts a cam action on the lug 28, thereby ejecting the clamp outwardly (or rightwardly in FIG. 10) from mechanism 33. Surface 41 on lug 28 forms a cam follower surface cooperable with the cam surface on wedge element 9 to achieve the clamp eject operation.

FIG. 9 shows the cutting plane of blade 11 in relation to the clamp planes of jaws 1 and 3 and the gripper elements 23 and 24. In FIG. 9 the plane of blade 11 is designated by numeral 43, the clamp plane of jaws 1 and 3 is designated by numeral 44, and the grip plane of gripper elements 23 and 24 is designated by numeral 47. Cutter plane 43 is located relatively close to clamp plane 44, but relatively remote from grip plane 47. Therefore, the severed fetal cord (in FIG. 10) will have an uncompressed terminal section 49 that can be readily viewed by the doctor for examination of the arteries and veins in the fetal cord section. This is an advantageous feature of the illustrated construction.

FIG. 1 shows the umbilical cord 31 inserted into the opened mechanism 33. Guard loops 8 and 26 on the jaws and gripper elements help to prevent inadvertant movement of the cord into the hinge structure cavity. The relative stiffness of hinge wall 5 (in relation to wall 7) is such that when jaw 1 is moved from the FIG. 1 open position to the FIG. 3 closed position the blade holder 2 remains essentially motionless relative to jaw 3.

Figure 4:
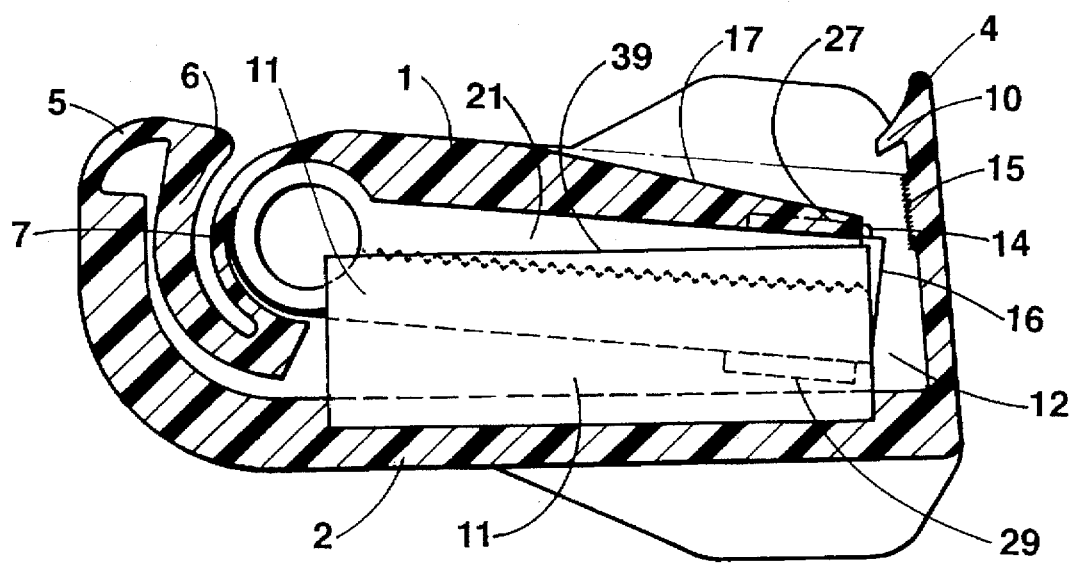
FIG. 4 is a sectional view taken generally on line 4—4 in FIG. 9.

However, when the jaws (and gripper elements) are brought together, as in FIG. 3, continued manual squeezing pressure on the mechanism brings blade holder 2 toward jaw 3, to the FIG. 4 position. Sharpened edge 39 on blade 11 severs the umbilical cord, but only after the cord is in a stabilized (controlled) position clamped at two points by the jaws 1 and 3, and the gripper elements 23 and 24. During the cord-severing operation blade edge 39 moves into a slot 21 in jaw 1.

FIG. 10 shows the blade in generally the same position as depicted in FIG. 4. During the cutting operation wedge block 9 ejects the fetal cord clamp 22 out of the clamp mechanism, as shown in FIG. 10.

Figure 5:
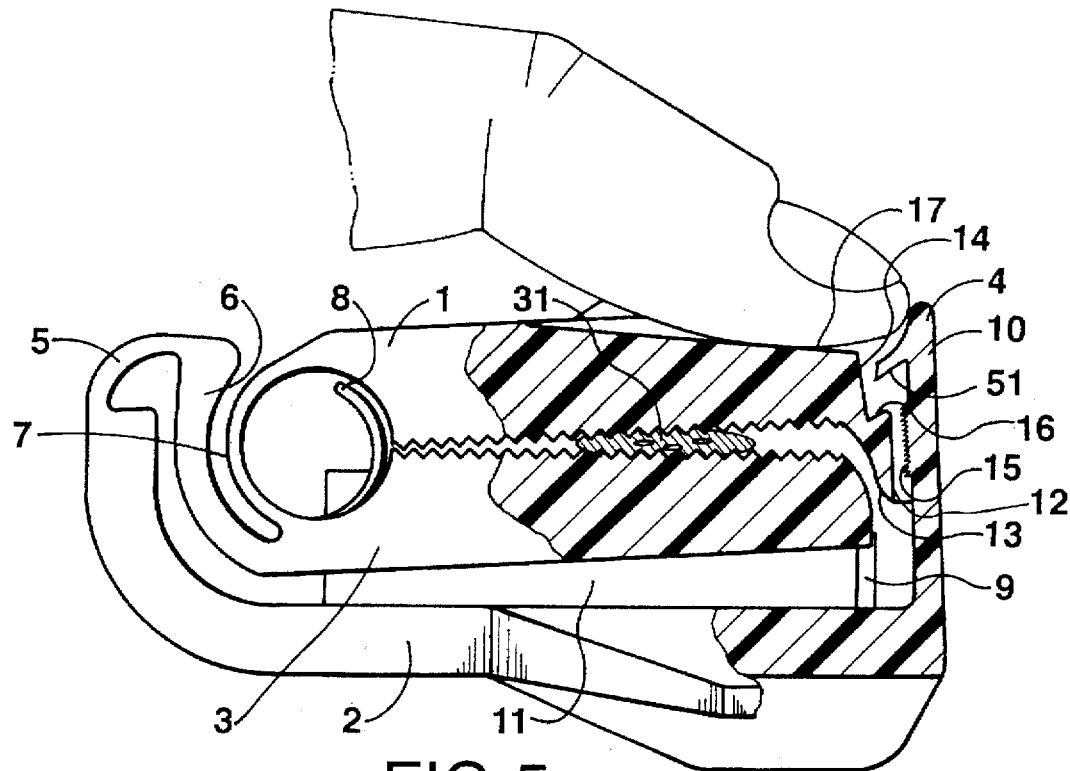
FIGS. 5 and 6 are partial sectional views taken in the same direction as FIG. 3, but showing the mechanism in different conditions of adjustment.
Figure 6:
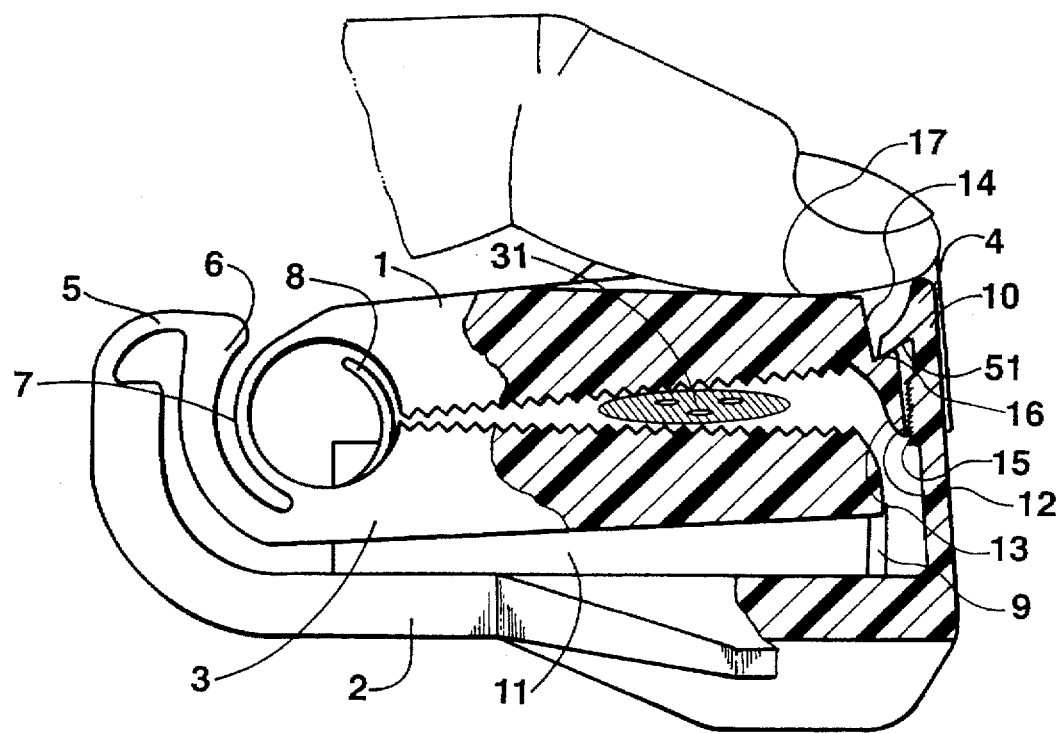

FIGS. 5 and 6 show a latch feature whereby the severed maternal umbilical cord can be partially unclamped from mechanism 33 to permit blood to be drawn therefrom.

The latch structure comprises an upstanding deflectable tongue 4 extending right angularly from the free end of blade holder 2. Tongue 4 has a plurality of locking teeth 15 adapted to selectively engage a locking detent 12 on the end surface of jaw 1, whereby jaw 1 can be retained in various positions of adjustment, to achieve various degrees of clamping engagement on the maternal cord. Tongue 4 is an integral plastic extension of blade holder 2, such that the connection between the tongue and blade holder is flexible, whereby the doctor can apply thumb pressure to the upper end of tongue 4 to adjust the locking action.

Complete separation of jaw 1 from jaw 3 is prevented by the interengagement of hook 51 on tongue 4 with shoulder 16 on the end surface of jaw, as shown in FIG. 6. The length of tongue 4 is such that the person's thumb can sense the upper end of tongue 4 to effect complete release of jaw 1 from the maternal cord section after the blood sample hs been taken, and it is no longer necessary to maintain the clamp action.

The adjustable latch action enables the mechanism to conform to a range of different umbilical cord thickness, and to respond to different conditions of the maternal cord required to take blood samples without losing control of the process.

The drawing shows a preferred form of the invention. The illustrated apparatus is believed to have several advantages as heretofore indicated. Other advantages and modifications suggested by the drawings and description can be achieved, while still practicing the invention. The mechanism is preferably formed as a plurality of low cost molded plastic components, whereby the mechanism is disposable.

What is claimed is:

1. A mechanism for cutting an umbilical cord, comprising:

a housing (33) that includes first and second jaws (1 and 2) hingedly connected together for relative movement between an open condition and a closed condition gripping an umbilical cord;

a fetal cord clamp (22) removably disposed within said housing, said clamp having clamp surfaces adapted to grip an umbilical cord when said jaws are in the closed position, whereby an umbilical cord is gripped at two separate grip planes spaced along the umbilical cord;

a blade holder (2) hingedly connected to said housing;

a cutter blade (11) carried by said holder for movement through an umbilical cord only after the umbilical cord is in the grip of said jaws and said clamp;

said housing (33) comprising a one piece plastic molding that includes said first and second jaws, and a first hinge wall (7) hingedly connecting said first and second jaws together;

said blade holder comprising a plastic arm structure having a second hinge wall (5) connected to said housing, whereby said blade holder can be swung toward the housing when the two jaws are in the closed position;

said housing and said blade holder being a one piece unitary molded construction.

2. The mechanism of claims 1, wherein said first hinge wall has a lesser resistance to flexure than said second hinge wall, whereby manual pressure on said mechanism is effective to close said jaws before the cutter blade can be moved to cut the umbilical cord.

3. The mechanism of claim 2, wherein said first hinge wall is an arcuate wall having an arcuate length of about one hundred thirty degrees, and said second hinge wall is an arcuate wall having an arcuate length of about ninety degrees.

4. The mechanism of claim 3, wherein said first arcuate hinge wall has a lesser thickness than said second arcuate hinge wall.

5. The mechanism of claim 3, and further comprising an arcuate connector wall (6) joining said first arcuate hinge wall to said second arcuate hinge wall; said connector wall being appreciably thicker than either of said first and second arcuate hinge walls.

6. A mechanism for cutting an umbilical cord, comprising:

a housing (33) that includes first and second jaws (1 and 2) hingedly connected together for relative movement between an open condition and a closed condition gripping an umbilical cord;

a fetal cord clamp (22) removably disposed within said housing, said clamp having clamp surfaces adapted to grip an umbilical cord when said jaws are in the closed condition, whereby an umbilical cord is gripped at two separate grip planes spaced along the umbilical cord;

a blade holder (2) hingedly connected to said housing;

a cutter blade (11) carried by said holder for movement through an umbilical cord only after the umbilical cord is in the grip of said jaws and said clamp;

said second jaw being located between said first jaw and said blade holder so that the cutter blade moves through the plane of said second jaw to sever an umbilical cord;

said blade holder comprising an elongated arm structure having a free and, a deflectable tongue (4) extending angularly from the free end of said arm structure;

said tongue having a plurality of locking teeth (15) thereon; said first jaw having a locking detent (12) in registry with said locking teeth, whereby when the first and second jaws are moved toward each other said locking detent is selectively engageable with different locking teeth, such that said first jaw can be retained in various positions of cord-gripping adjustment relative to said second jaw;

said first jaw having an external shoulder (16) facing said deflectable tongue; said tongue having a hook (51) adapted to interengage said shoulder when the jaws are separated by a distance sufficient to permit to be taken from a severed umbilical cord; said tongue having a free end that can be contacted by a person's thumb to deflect said tongue away from said shoulder on said first jaw.

7. A mechanism for cutting am umbilical cord, comprising:

a housing (33) that includes first and second jaws (1 and 2) hingedly connected together for relative movement between an open condition and a closed condition gripping an umbilical cord;

a fetal cord clamp (22) removably disposed within said housing, said clamp having clamp surfaces adapted to grip an umbilical cord when said jaws are in the closed condition, whereby an umbilical cord is gripped along two separate grip planes at different points on the umbilical cord;

a blade holder (2) hingedly connected to said housing;

a cutter blade (11) carried by said holder for movement through an umbilical cord only after the umbilical cord is in the grip of said jaws and said clamp; and a cam means (9) carried by said second jaw in the path of said fetal cord clamp associated with cord-cutting movement of said blade; said cam means being oriented to exert an ejection force on the clamp during the cord-cutting operation.

8. The mechanism of claim 7, wherein said jaws are engageable with the umbilical cord in a first grip plane, and said fetal clamp is engageable with the umbilical cord in a second grip plane; said cutter blade being located in a third plane located between said first and second grip planes;

said third plane being relatively close to said first grip plane and relatively remote from said second grip plane, so that when the fetal cord clamp is separated from said housing the severed fetal cord will have an uncompressed terminal section that can be readily viewed for examination of the arteries and veins in the fetal cord.

* * * * *